United States Patent
Liu et al.

(10) Patent No.: US 10,482,350 B2
(45) Date of Patent: Nov. 19, 2019

(54) DROWSINESS DETECTION APPARATUS AND DROWSINESS DETECTION METHOD THEREOF

(71) Applicant: Wistron Corp., New Taipei (TW)

(72) Inventors: Zhen-Te Liu, New Taipei (TW); Yu-Yen Chen, New Taipei (TW)

(73) Assignee: Wistron Corp., New Taipei (TW)

( * ) Notice: Subject to any disclaimer, the term of this patent is extended or adjusted under 35 U.S.C. 154(b) by 26 days.

(21) Appl. No.: 15/817,101

(22) Filed: Nov. 17, 2017

(65) Prior Publication Data
US 2019/0065898 A1 Feb. 28, 2019

(30) Foreign Application Priority Data
Aug. 28, 2017 (TW) .............................. 106129147 A (51) Int. Cl.
| | | |
|---|---|---|
| *G06K 9/62* | (2006.01) | |
| *G08B 21/06* | (2006.01) | |
| *G06K 9/00* | (2006.01) | |
| *A61B 5/18* | (2006.01) | |
| *B60Q 9/00* | (2006.01) | |

(Continued)

(52) U.S. Cl.
CPC .......... *G06K 9/6212* (2013.01); *A61B 5/0077* (2013.01); *A61B 5/1103* (2013.01); *A61B 5/18* (2013.01); *B60Q 9/00* (2013.01); *G06K 9/0053* (2013.01); *G06K 9/0061* (2013.01); *G06K 9/00275* (2013.01); *G08B 21/06* (2013.01)

(58) Field of Classification Search
None
See application file for complete search history.

(56) References Cited

U.S. PATENT DOCUMENTS 5,218,387 A * 6/1993 Ueno .................... A61B 3/113
351/210
5,859,921 A * 1/1999 Suzuki ............... G06K 9/00268
382/118

(Continued)

OTHER PUBLICATIONS

Chien-Chung Wu et al., "Real-time Driver Attention Monitoring and Recording System," 2015 Conference on Information Technology and Applications in Outlying Islands, 2015, pp. 161-167, Taiwan.

(Continued)

*Primary Examiner* — Fayyaz Alam (57) ABSTRACT

A drowsiness detection apparatus is provided. The drowsiness detection apparatus: an image capturing unit, an alarm apparatus, and a drowsiness determination circuit. The image capturing unit is configured to repeatedly capture a plurality of facial images of a user. The drowsiness determination circuit is configured to obtain an eye region from a current image of the facial images, calculate a vertical histogram of the eye region, and determine an eye part from the eye region according to the vertical histogram. The drowsiness determination circuit further compares the pixel height of the eye part with a closed-eye pixel threshold to perform closed-eye detection, and performs drowsiness detection on the user according to the results of the closed-eye detection. When the result of the drowsiness detection indicates that the user is drowsy, the drowsiness determination circuit transmits a control signal to the alarm apparatus to sound an alarm.

12 Claims, 4 Drawing Sheets

(51) Int. Cl.
*A61B 5/00* (2006.01)
*A61B 5/11* (2006.01)

(56) References Cited

U.S. PATENT DOCUMENTS

| | | | | |
|---|---|---|---|---|
| 5,878,156 | A * | 3/1999 | Okumura | G06K 9/00268 |
| | | | | 340/575 |
| 6,419,638 | B1 * | 7/2002 | Hay | A61B 3/0025 |
| | | | | 600/558 |
| 6,717,518 | B1 * | 4/2004 | Pirim | B60R 1/04 |
| | | | | 340/576 |
| 9,082,012 | B2 * | 7/2015 | Shimura | G06K 9/00845 |
| 9,955,903 | B2 * | 5/2018 | Kobetski | A61B 5/18 |
| 2007/0036438 | A1 * | 2/2007 | Thakur | G06K 9/0061 |
| | | | | 382/190 |
| 2010/0036290 | A1 * | 2/2010 | Noguchi | A61B 5/165 |
| | | | | 600/595 |

OTHER PUBLICATIONS

I-Ling Tsai et al., "Drowsiness Detection and Warning for Vehicle Active Safety," Journal of Information, Technology and Science, 2013, 21 pages, Taiwan.

* cited by examiner

DROWSINESS DETECTION APPARATUS AND DROWSINESS DETECTION METHOD THEREOF

CROSS REFERENCE TO RELATED APPLICATIONS

This Application claims priority of Taiwan Patent Application No. 106129147, filed on Aug. 28, 2017, the entirety of which is incorporated by reference herein.

BACKGROUND OF THE INVENTION

Field of the Invention

The present invention relates to drowsiness detection apparatuses, and, in particular, to a drowsiness detection apparatus and drowsiness detection method thereof.

Description of the Related Art

With regard to mobile safety systems, advanced driver assistance systems (ADAS) for exterior circumstances and drowsiness detection systems for interior circumstances have been developed to assist the driver. The drowsiness detection system may sound an alarm to awaken the driver upon detecting drowsiness or poor mental conditions of the driver. However, it is very difficult to detect the physical or mental conditions of the driver. Currently, contact techniques may directly measure parameters such as the heart rate or blood oxygen of the driver, and non-contact techniques may detect the outline of the driver. For example, with regard to non-contact techniques, the closed/open conditions of eyes of the driver can be detected to determine whether the driver is drowsy. However, a computer system does not realize the closed/open conditions of the eyes of the driver, and thus the eye size of the driver in the captured images can be used to determine the drowsiness of the driver. It should be noted that every driver may have an individual eye size, and the eye size may vary due to different driving positions. Thus, it is difficult to define an appropriate threshold for the eye size for conventional techniques. Accordingly, conventional techniques cannot correctly determine the eyes of the driver from the captured images, resulting in a lower accuracy of drowsiness detection.

Therefore, there is demand for a drowsiness detection apparatus and a drowsiness detection method to solve the aforementioned problem.

BRIEF SUMMARY OF THE INVENTION

A detailed description is given in the following embodiments with reference to the accompanying drawings.

In an exemplary embodiment, a drowsiness detection apparatus is provided. The drowsiness detection apparatus includes an image capturing unit, an alarm apparatus, and a drowsiness determination circuit. The image capturing unit is configured to repeatedly capture a plurality of facial images of a user. The drowsiness determination circuit is configured to obtain an eye region from a current image of the facial images, calculate a vertical histogram of the eye region, and determine an eye part from the eye region according to the vertical histogram. The drowsiness determination circuit further compares a pixel height of the eye part with a closed-eye pixel threshold to perform closed-eye detection, and performs drowsiness detection on the user according to the results of the closed-eye detection. When the result of the drowsiness detection indicates that the user is drowsy, the drowsiness determination circuit transmits a control signal to the alarm apparatus to raise an alarm.

In another exemplary embodiment, a drowsiness detection method for use in a drowsiness detection apparatus is provided. The drowsiness detection apparatus comprises an image capturing unit and an alarm sound. The method includes the steps of: utilizing the image capturing unit to repeatedly capture a plurality of facial images of a user; obtaining an eye region from a current image of the facial images; calculating a vertical histogram of the eye region; determining an eye part from the eye region according to the vertical histogram; comparing a pixel height of the eye part with a closed-eye pixel threshold to perform closed-eye detection; performing drowsiness detection on the user according to the results of the closed-eye detection; and transmitting a control signal to the alarm apparatus to raise an alarm when the result of the drowsiness detection indicates that the user is drowsy.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
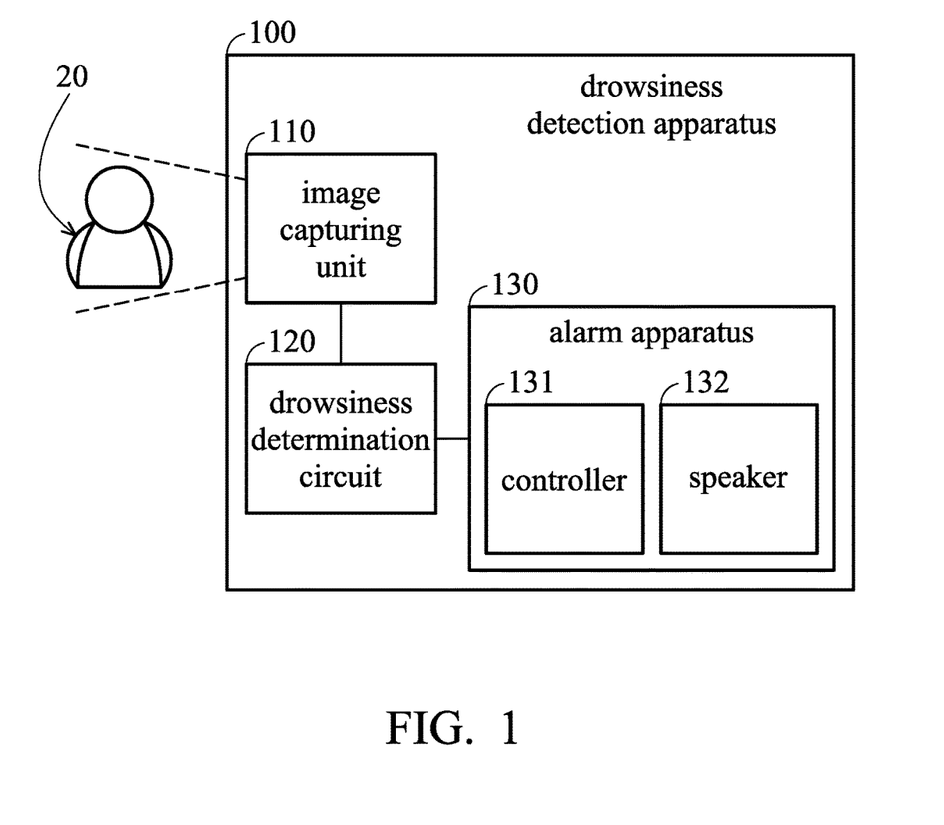
FIG. 1 is a schematic block diagram of a drowsiness detection apparatus in accordance with an embodiment of the invention.

FIG. 1 is a schematic block diagram of a drowsiness detection apparatus in accordance with an embodiment of the invention.

As illustrated in FIG. 1, the drowsiness detection apparatus 100 may perform drowsiness detection on a user 20. For example, the drowsiness detection apparatus 100 can be installed in the in-vehicle system of a car for detecting the closed/open conditions of the eyes of the driver (i.e. user 20) and determining whether the driver is in a good mental condition.

In an embodiment, the drowsiness detection apparatus 100 may include an image capturing apparatus 110, a drowsiness determination circuit 120, and an alarm apparatus 130.

The image capturing apparatus 110 may be a camera including charge-coupled device (CCD) sensors or complementary metal-oxide semiconductor (CMOS) sensors. The image capturing apparatus 110 is configured to repeatedly shoot the face of a target (e.g. the driver) to generate an image signal.

The drowsiness determination circuit 120 is configured to receive the image signal from the image capturing apparatus 110, and analyze the received image signal to determine the drowsiness of the user 20. The details for the drowsiness determination procedure will be described later. For example, the drowsiness determination circuit 120 may be an application-specific integrated circuit (ASIC), a field-programmable gate array (FPGA), or specific logic circuits, but the invention is not limited thereto. In some embodiments, the drowsiness determination circuit 120 can be implemented by a central processing unit (CPU), a digital signal processor (DSP), or an image signal processor (ISP), but the invention is not limited thereto.

The alarm apparatus 130 may include a controller 131 and a speaker 132. The controller 131 is configured to receive a control signal from the drowsiness determination circuit 120, and control the speaker 132 to raise a corresponding alarm sound in response to the control signal.

When the drowsiness determination circuit 120 determines that the user 20 is drowsy, the drowsiness determination circuit 120 may send a control signal to the alarm apparatus 130. Meanwhile, the alarm apparatus 130 may sound an alarm to awaken or notify the user 20 according to the control signal from the drowsiness determination circuit 120.

Figure 2A:
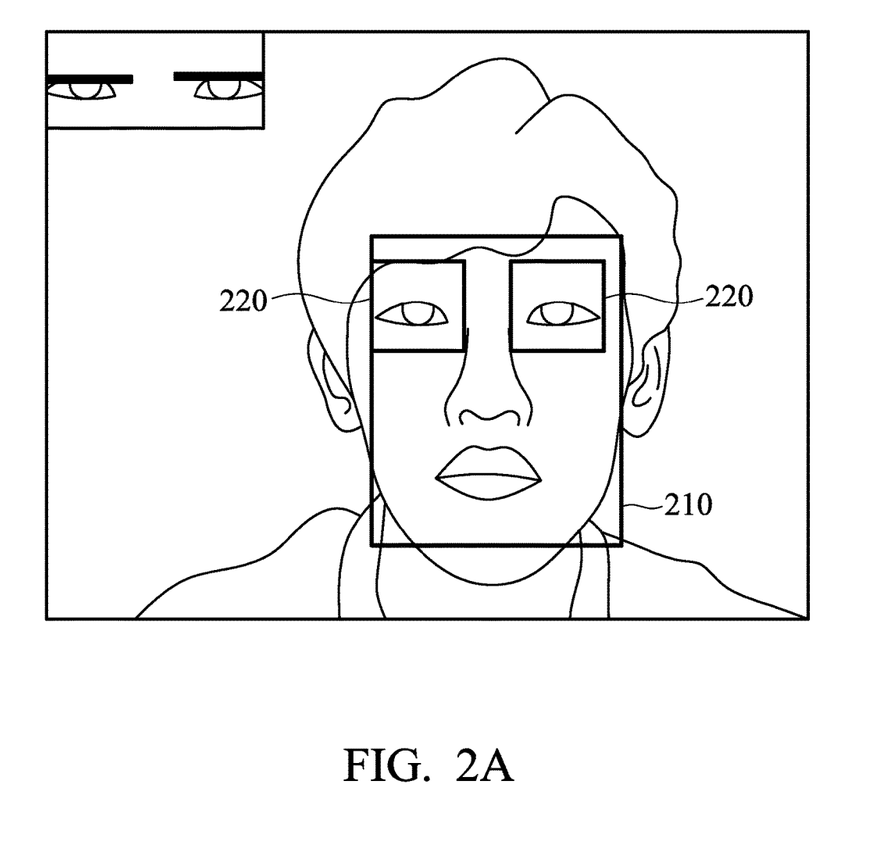
FIG. 2A is a diagram of an image signal in accordance with an embodiment of the invention.

FIG. 2A is a diagram of an image signal in accordance with an embodiment of the invention.

In an embodiment, when the drowsiness determination circuit 120 has received the image signal from the image capturing apparatus 110, the drowsiness determination circuit 120 may analyze the signal to determine a face region 210 of the user 20, and determines an eye region 220 from the face region 210. The eye region 220 can also be regarded as a region of interest (ROI). Then, the drowsiness determination circuit 120 may calculate a vertical histogram of the eye region 220. It should be noted that the eye region 220 includes the eyes and the surrounding region thereof. That is, the eye region may include an eye-glass frame, eyebrows, and eyelids.

Figure 2B:
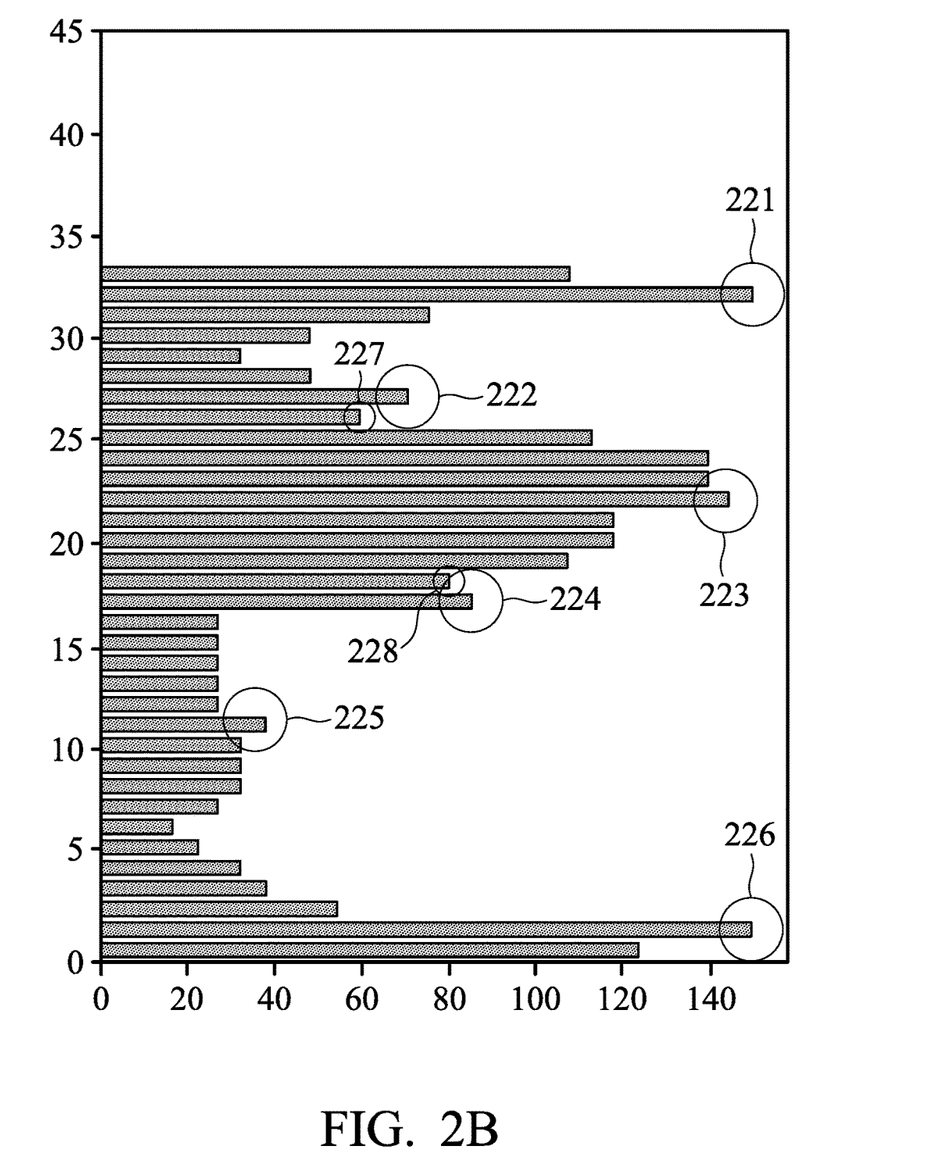
FIG. 2B is a diagram of the vertical histogram of the eye region in the image signal in accordance with an embodiment of the invention.

FIG. 2B is a diagram of the vertical histogram of the eye region in the image signal in accordance with an embodiment of the invention.

Specifically, since the eye region 220 has a small portion in the image signal, thus numbers of pixels in each row of the eye region 220 can be calculated. For example, pixels in human eyes are generally black and white. That is, a pixel having a grayscale value smaller than a predetermined threshold can be determined as a black pixel. In addition, a pixel having a grayscale value greater than the predetermined threshold can be determined as a white pixel. However, the eye region 220 (i.e. ROI) may include non-human-eye components such as the eye-glass frame, eyebrows, and eyelids. Accordingly, the drowsiness determination circuit 120 may calculate the number of pixels in each row of the eye region 220, thereby generating the vertical histogram. The horizontal axis of FIG. 2A indicates the number of black pixels, and the vertical axis indicates the row number in the eye region 220. In the invention, human eyes can be filtered from the eye region 220 using the vertical histogram and subsequent determination procedure.

In an embodiment, the drowsiness determination circuit 120 may determine a plurality of relative peak values from the vertical histogram of the eye region 220. For example, when the difference of the numbers of black pixels of a specific row and its neighboring rows is greater than a predetermined value, it is determined that the specific row has a relative peak value, such as relative peak values 221~226. Then, the drowsiness determination circuit 120 may find a plurality of effective peak values from the relative peak values.

Specifically, the drowsiness determination circuit 120 may determine the maximum relative value from the relative peak values, and set a threshold according to the maximum relative peak value. For example, the threshold may be calculated by multiplying the maximum relative peak value with a predetermined factor (e.g. 2/3). It should be noted that the predetermined factor can be adjusted according to practical conditions.

Referring to FIG. 2B, the relative peak value 221 is the maximum value between the relative peak values 221~226, and thus the drowsiness determination circuit 120 may determine that the relative peak value 221 is the maximum relative value. Then, the drowsiness determination circuit 120 may multiply the maximum relative value with the predetermined factor to obtain a threshold for filtering the relative peak values 221~226. For example, given that the predetermined factor is 2/3, the relative peak values 221, 223, and 226 are filtered from the relative peak values 221~226. The drowsiness determination circuit 120 may determine the relative peak values 221, 223, and 226 as effective peak values.

After obtaining the effective peak values, the drowsiness determination circuit 120 may further determine the eye region using the effective peak values. For example, the drowsiness determination circuit 120 may calculate a region associated with each of the effective peak values, and determine the largest region as the eye region which includes pixels of the eyes. Specifically, the definition of the region associated with an effective peak value is the region between the effective peak value and its neighboring valley values (i.e. upper and lower valley values closest to the effective peak value). Referring to the example of FIG. 2B, the effective peak value 223 has neighboring valley values 227 and 228, and the region between the effective peak value 223 and its neighboring valley values 227 and 228 may have the largest region. Accordingly, the drowsiness determination circuit 120 may determine the region between the valley values 227 and 228 as the eye part, and calculate the pixel height (e.g. in pixels) of the eye part. In an embodiment, since the image capturing apparatus 110 repeatedly captures facial images of the user 20, the drowsiness determination circuit 120 may further calculates the number of images of the eye region. That is, the drowsiness determination circuit 120 may detect the images (e.g. eye images) having the eye region with a calculated pixel height, and calculates the number of the eye images. When the number of the eye images is less than a predetermined number, the drowsiness determination circuit 120 may store the pixel height of the eye part of the current image. When the number of the eye images reaches the predetermined number (e.g. 20 or 300, not limited), the drowsiness determination circuit 120 may determine the maximum pixel height of the eye part within the predetermined number of eye images, and update the value of the maximum pixel height. It should be noted that the predetermined number can be adjusted according to practical conditions.

Specifically, the drowsiness determination circuit 120 may detect the status of the eye region of the driver who is driving the vehicle. However, the driver may perform various actions on the driving seat, such as drinking coffee, reaching for the glove compartment, adjusting the air conditioner vent, adjusting the air temperature, setting the GPS, talking with the passengers, or checking SMS messages, and the pixel height of the eye part in the capture images may vary due to different actions. Accordingly, if the predetermined number of eye images is too small, the maximum pixel height of the eye part obtained by the drowsiness determination circuit 120 may be the pixel height of the eye part while performing one of the aforementioned actions rather than that of the eye part while driving the vehicle.

In an embodiment, the drowsiness determination circuit 120 may update the maximum pixel height of the eye part each time the drowsiness determination circuit 120 has obtained the predetermined number of eye images (i.e. a cycle). For example, when a predetermined number (e.g. 20 or 300, not limited) of eye images has been accumulated, the drowsiness determination circuit 120 may find the maximum pixel height of the eye part within the predetermined number of eye images, and update the maximum pixel height. It should be noted that the updated maximum pixel height is used for drowsiness detection in the predetermined number of subsequent eye images. If the number of accumulated eye images of the current cycle is less than the predetermined number, the drowsiness determination circuit 120 may use the maximum pixel height of the eye part in the previous cycle for eye state detection (i.e. detecting open and closed eyes).

In the embodiment, after obtaining the maximum pixel height of the eye part, the drowsiness determination circuit 120 may determine whether a closed-eye pixel threshold has been set. For example, if the drowsiness determination circuit 120 determines that the pixel height of the eye part in the current image is less than the closed-eye pixel threshold, the drowsiness determination circuit 120 may accumulate a closed-eye image count by 1. When the closed-eye image count has reached an upper threshold within a predetermined period, the drowsiness determination circuit 120 may determine that the user is drowsy, and transmit a control signal to the alarm apparatus 130 to sound an alarm to notify the user.

Specifically, if the closed-eye pixel threshold is not set yet (e.g. the drowsiness detection apparatus 100 is just booting up), the drowsiness determination circuit 120 may set the maximum pixel height of the eye part in the current cycle as the closed-eye pixel threshold. That is, drowsiness detection is not performed in the first cycle. If the closed-eye pixel threshold is already set, the drowsiness determination circuit 120 may determine the difference between the calculated maximum pixel height and the closed-eye pixel threshold is larger than or equal to a predetermined value X. If so, the drowsiness determination circuit 120 may update the closed-eye pixel threshold with the calculated maximum pixel height of the eye part in the current cycle. If not, the drowsiness determination circuit 120 will not update the closed-eye pixel threshold.

For example, when the closed-eye pixel threshold is set, the drowsiness determination circuit 120 has to determine whether the head of the driver is moving using the predetermined value X as a threshold. That is, if the motion of the head of the driver is greater than or equal to the predetermined value X, it indicates that the head of the driver is moving, and thus the closed-eye pixel threshold should be updated. If the motion of the head of the driver is less than the predetermined value X, it indicates that the head of the driver is stationary or has little motion, and thus it is not necessary to update the closed-eye pixel threshold.

Table 1 illustrates examples of various closed-eye pixel threshold in different conditions in accordance with an embodiment of the invention.

TABLE 1

| Image No. | Driver's Action | Max Pixel Height of Eye Part | Closed-eye Pixel Threshold |
|---|---|---|---|
| 0~300 | Driving | 12 | None |
| 301~600 | Driving | 12 | 12 |
| 601~900 | looking up | 9 | 12 |
| 901~1200 | Driving | 11 | 9 |
| 1201~1500 | moving backward | 8 | 11 |
| 1501~1800 | Driving | 10 | 8 |
| 1801~2100 | Driving | 12 | 10 |

Referring to Table 1, in the embodiment, the predetermined value X is 2 and the number of images in each cycle is 300. It should be noted that the predetermined value and the number of images given are for description, and the invention is not limited thereto.

In the first cycle from image 0 to image 300, the drowsiness detection apparatus 100 has just booted up, and the driver is driving well, and the closed-eye pixel threshold is not set yet.

In the second cycle from image 301 to image 600, the driver is still driving well. Since the closed-eye pixel threshold is not set in the first cycle, the drowsiness determination circuit 120 may set the calculated maximum pixel height (e.g. 12) of the first cycle as the closed-eye pixel threshold after calculation of the last image of the first cycle (i.e. image 300), and the closed-eye pixel threshold is for closed-eye detection in the second cycle.

After calculation of the last image of the second cycle (i.e. image 600), the drowsiness determination circuit 120 may compare the current closed-eye pixel threshold (e.g. 12) with the calculated maximum pixel height (e.g. 12) of the second cycle (i.e. from image 301 to image 600). Since the difference between the current closed-eye pixel threshold and the calculated pixel height of the second cycle is 0, the drowsiness determination circuit 120 will not update the closed-eye pixel threshold, and still use the current closed-eye pixel threshold for closed-eye detection in the third cycle (i.e. from image 601 to image 900).

In the third cycle from image 601 to image 900, the driver is looking up. After calculation of the last image of the third cycle (i.e. image 900), the drowsiness determination circuit 120 may compare the current closed-eye pixel threshold (e.g. 12) with the calculated maximum pixel height (e.g. 9) of the third cycle (i.e. from image 601 to image 900). Since the difference between the current closed-eye pixel threshold and the calculated pixel height of the third cycle is 3 that is larger than the predetermined value X, the drowsiness determination circuit 120 will update the closed-eye pixel threshold to 9 that used for closed-eye detection in the fourth cycle (i.e. from image 901 to image 1200).

In the fourth cycle from image 901 to image 1200, the driver is driving well. After calculation of the last image of the fourth cycle (i.e. image 1200), the drowsiness determination circuit 120 may compare the current closed-eye pixel threshold (e.g. 9) with the calculated maximum pixel height (e.g. 11) of the fourth cycle (i.e. from image 901 to image 1200). Since the difference between the current closed-eye pixel threshold and the calculated pixel height of the third cycle is 2 that is equal to the predetermined value X, the drowsiness determination circuit 120 will update the closed-eye pixel threshold to the maximum pixel height (e.g. 11) of the eye region in the fourth cycle, and the updated closed-eye pixel threshold is used for closed-eye detection in the fifth cycle (i.e. from image 1201 to image 1500).

In the fifth cycle from image 1201 to image 1500, the driver is moving backward (e.g. adjusting the driver's seat). After calculation of the last image of the fifth cycle (i.e. image 1500), the drowsiness determination circuit 120 may compare the current closed-eye pixel threshold (e.g. 11) with the calculated maximum pixel height (e.g. 8) of the fifth cycle (i.e. from image 1201 to image 1500). Since the difference between the current closed-eye pixel threshold and the calculated pixel height of the third cycle is 3 that is greater than the predetermined value X, the drowsiness determination circuit 120 will update the closed-eye pixel threshold to the maximum pixel height (e.g. 8) of the eye region in the fifth cycle, and the updated closed-eye pixel threshold is used for closed-eye detection in the sixth cycle (i.e. from image 1501 to image 1800).

In the sixth cycle from image 1501 to image 1800, the driver is driving well. After calculation of the last image of the sixth cycle (i.e. image 1800), the drowsiness determination circuit 120 may compare the current closed-eye pixel threshold (e.g. 8) with the calculated maximum pixel height (e.g. 10) of the sixth cycle (i.e. from image 1501 to image 1800). Since the difference between the current closed-eye pixel threshold and the calculated pixel height of the third cycle is 2 that is equal to the predetermined value X, the drowsiness determination circuit 120 will update the closed-eye pixel threshold to the maximum pixel height (e.g. 10) of the eye region in the sixth cycle, and the updated closed-eye pixel threshold is used for closed-eye detection in the seventh cycle (i.e. from image 1801 to image 2100).

In the seventh cycle from image 1801 to image 2100, the driver is driving well. After calculation of the last image of the seventh cycle (i.e. image 2100), the drowsiness determination circuit 120 may compare the current closed-eye pixel threshold (e.g. 10) with the calculated maximum pixel height (e.g. 12) of the seventh cycle (i.e. from image 1801 to image 2100). Since the difference between the current closed-eye pixel threshold and the calculated pixel height of the third cycle is 2 that is equal to the predetermined value X, the drowsiness determination circuit 120 will update the closed-eye pixel threshold to the maximum pixel height (e.g. 12) of the eye region in the sixth cycle, and the updated closed-eye pixel threshold is used for closed-eye detection in the subsequent cycle.

Figure 3:
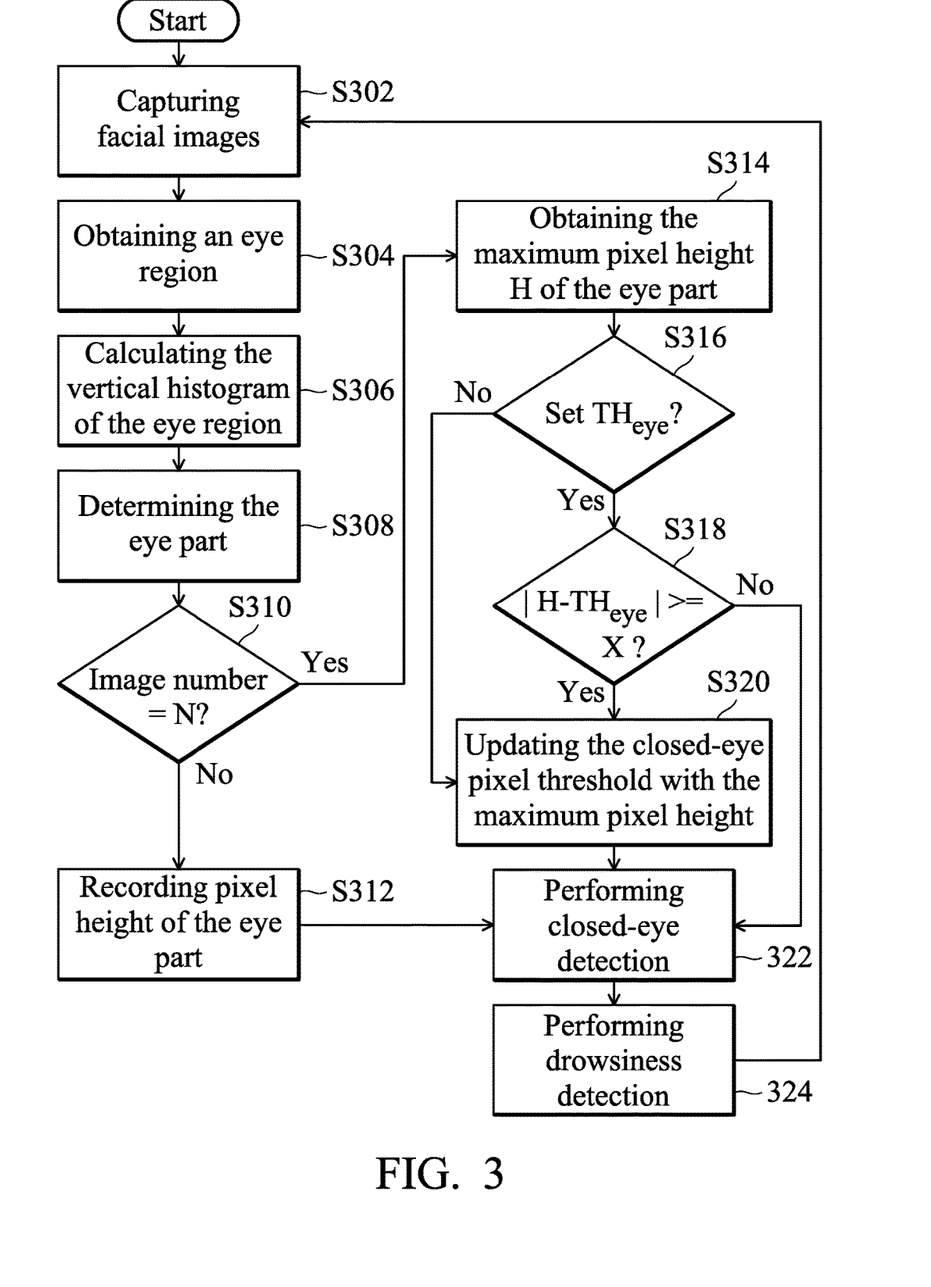
FIG. 3 is a flow chart of a drowsiness detection method in accordance with an embodiment of the invention.

FIG. 3 is a flow chart of a drowsiness detection method in accordance with an embodiment of the invention.

In step S302, the image capturing apparatus 110 is utilized to repeatedly capture a plurality of facial images of a user.

In step S304, an eye region is obtained from a current image of the facial images. For example, the drowsiness determination circuit 120 may calculate a face region from the current image, and determine an eye region from the face region, wherein techniques for determining the face region and eye region are well-known to those having ordinary skill in the art, and thus the details will be omitted here.

In step S306, a vertical histogram of the eye region is calculated. For example, the drowsiness determination circuit 120 may calculate the number of black pixels in each row of the eye region to generate the vertical histogram.

In step S308, an eye part is determined from the eye region according to the vertical histogram. For example, the drowsiness determination circuit 120 may obtain a plurality of relative peak values from the vertical histogram of the eye region, and determine the maximum relative peak value from the relative peak values, and filter a plurality of effective peak values from the relative peak values according to the maximum relative peak value, and determine the maximum region between the effective peak values as the eye part.

In step S310, it is determined whether the number of accumulated facial images has reached a predetermined number. If so, step S314 is performed. Otherwise, step S312 is performed.

In step S312, pixel height of the eye part is recorded. For example, the drowsiness determination circuit 120 periodically performs the closed-eye detection on the eye part of the user every cycle, and each cycle has a fixed number of images. In addition, the maximum pixel height is the maximum value of pixel heights of the eye part in the facial images in each cycle. Accordingly, after calculation of the last image of each cycle, the maximum pixel height for the cycle can be determined.

In step S314, a maximum pixel height H of the eye part is obtained.

In step S316, it is determined whether a closed-eye pixel threshold is calculated. If so, step S318 is performed. Otherwise, step S320 is performed.

In step S318, it is determined whether the absolute difference between the maximum pixel height H and the closed-eye pixel threshold $TH_{eye}$ is greater than or equal to a predetermined value X. If so, step S320 is performed. Otherwise, step S322 is performed.

In step S322, closed-eye detection is performed. For example, if the pixel height of the eye part is lower than the closed-eye pixel threshold, the drowsiness determination circuit 120 may determine that the eye part of the current image is in a closed-eye state. If the pixel height of the eye part is higher than or equal to the closed-eye pixel threshold, the drowsiness determination circuit 120 may determine that the eye part of the current image is in an open-eye state.

In step S324, drowsiness detection is performed. For example, if the drowsiness determination circuit 120 determines that the pixel height of the eye part of the current image is lower than the closed-eye pixel threshold, a closed-eye image count is accumulated by 1. When the closed-eye image count has reached an upper threshold within a predetermined period, the drowsiness determination circuit 120 may determine that the user is drowsy, and transmit a control signal to the alarm apparatus 130 to sound an alarm to notify the user.

In view of the above, a drowsiness detection apparatus and a drowsiness detection method is provided in the invention. The drowsiness detection apparatus and the drowsiness detection method are capable of dynamically adjusting the threshold of the eye part in the captured images. Thus, even if the driver alternates his or her driving positions, the drowsiness detection apparatus and the drowsiness detection method may calibrate the threshold corresponding to prevent from misdetection.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A drowsiness detection apparatus, comprising:
   an image sensor, configured to repeatedly capture a plurality of facial images of a user;
   an alarm apparatus; and a processor, configured to obtain an eye region from a current image of the facial images, calculate a vertical histogram of the eye region, and determine an eye part from the eye region according to the vertical histogram, wherein the processor further compares a pixel height of the eye part with a closed-eye pixel threshold to perform closed-eye detection, and performs drowsiness detection on the user according to results of the closed-eye detection; and wherein when the result of the drowsiness detection indicates that the user is drowsy, the processor transmits a control signal to the alarm apparatus to sound an alarm, wherein the processor calculates a maximum pixel height of the eye part in the facial images within a current period, and determines whether to update the closed-eye pixel threshold according to a difference between the maximum pixel height and the closed-eye pixel threshold.

2. The drowsiness detection apparatus as claimed in claim 1, wherein when the difference between the maximum pixel height and the closed-eye pixel threshold is larger than or equal to a predetermined value, the processor updates the closed-eye pixel threshold with the maximum pixel height; and wherein when the difference between the maximum pixel height and the closed-eye pixel threshold is less than the predetermined value, the processor does not update the closed-eye pixel threshold.

3. The drowsiness detection apparatus as claimed in claim 1, wherein when the pixel height of the eye part in the current image is less than the closed-eye pixel threshold, the processor determines that the eye part in the current image is in a closed-eye state; and wherein when the pixel height of the eye part in the current image is larger than or equal to the closed-eye pixel threshold, the processor determines that the eye part in the current image is in an open-eye state.

4. The drowsiness detection apparatus as claimed in claim 3, wherein the processor further accumulates the number of facial images having the eye part in the closed-eye state within a predetermined period; and wherein when the number exceeds a predetermined number, the processor transmits the control signal to the alarm apparatus to raise the alarm.

5. The drowsiness detection apparatus as claimed in claim 1, wherein the processor calculates a number of black pixels in each row of the eye region to generate the vertical histogram.

6. The drowsiness detection apparatus as claimed in claim 5, wherein the processor obtains a plurality of relative peak values from the vertical histogram, determines a maximum relative peak value from the relative peak values, and filters a plurality of effective peak values from the relative peak values; and wherein the processor determines a maximum region between the effective peak values as the eye part.

7. A drowsiness detection method, for use in a drowsiness detection apparatus, wherein the drowsiness detection apparatus comprises an image sensor and an alarm apparatus, the method comprising:

utilizing the image sensor to repeatedly capture a plurality of facial images of a user;

obtaining an eye region from a current image of the facial images;

calculating a vertical histogram of the eye region;

determining an eye part from the eye region according to the vertical histogram;

comparing a pixel height of the eye part with a closed-eye pixel threshold to perform closed-eye detection;

calculating a maximum pixel height of the eye part in the facial images within a current period;

determining whether to update the closed-eye pixel threshold according to a difference between the maximum pixel height and the closed-eye pixel threshold;

performing drowsiness detection on the user according to the results of the closed-eye detection; and transmitting a control signal to the alarm apparatus to raise an alarm when the result of the drowsiness detection indicates that the user is drowsy.

8. The method as claimed in claim 7, further comprising:

when the difference between the maximum pixel height and the closed-eye pixel threshold is larger than or equal to a predetermined value, updating closed-eye pixel threshold with the maximum pixel height;

wherein when the difference between the maximum pixel height and the closed-eye pixel threshold is less than the predetermined value, skipping updating the closed-eye pixel threshold.

9. The method as claimed in claim 7, further comprising:

when the pixel height of the eye part in the current image is less than the closed-eye pixel threshold, determining that the eye part in the current image is in a closed-eye state; and when the pixel height of the eye part in the current image is larger than or equal to the closed-eye pixel threshold, determining that the eye part in the current image is in an open-eye state.

10. The method as claimed in claim 9, further comprising:

calculating a number of facial images having the eye part in the closed-eye state within a predetermined period;

wherein when the number exceeds a predetermined number, transmitting the control signal the alarm apparatus to raise the alarm.

11. The method as claimed in claim 7, further comprising:

calculating a number of black pixels in each row of the eye region to generate the vertical histogram.

12. The method as claimed in claim 11, further comprising:

obtaining a plurality of relative peak values from the vertical histogram;

determining a maximum relative peak value from the relative peak values;

filtering a plurality of effective peak values from the relative peak values; and determining a maximum region between the effective peak values as the eye part.

* * * * *